United States Patent [19]

Cragoe, Jr. et al.

[11] 4,189,496

[45] * Feb. 19, 1980

[54] 2,3-DIHYDRO-5-THIENYLMETHYL AND FURYLMETHYL-6-SUBSTITUTED AND 6,7-DISUBSTITUTED-BENZOFURAN-2-CARBOXYLIC ACID

[75] Inventors: Edward J. Cragoe, Jr.; William F. Hoffman, both of Lansdale; Otto W. Woltersdorf, Jr., Chalfont, all of Pa.

[73] Assignee: Merck & Co., Inc., Rahway, N.J.

[*] Notice: The portion of the term of this patent subsequent to Apr. 18, 1995, has been disclaimed.

[21] Appl. No.: 878,503

[22] Filed: Feb. 16, 1978

[51] Int. Cl.² .................... A01N 9/00; A01N 9/28; C07D 333/24; C07D 307/77
[52] U.S. Cl. .................... 424/275; 424/285; 260/346.22; 549/60
[58] Field of Search ............. 260/332.2 A, 332.3 H; 424/275, 285

[56] References Cited

U.S. PATENT DOCUMENTS

| | | | |
|---|---|---|---|
| 4,085,117 | 4/1978 | Cragoe et al. | 260/332.2 A |
| 4,087,542 | 5/1978 | Cragoe et al. | 260/332.2 A |
| 4,100,294 | 7/1978 | Cragoe et al. | 260/332.2 A |

*Primary Examiner*—A. Siegel
*Attorney, Agent, or Firm*—Michael C. Sudol, Jr.; Harry E. Westlake, Jr.

[57] ABSTRACT

2,3-Dihydro-6,7-disubstituted-5-thienylmethyl or furylmethyl benzofuran-2-carboxylic acids, the pharmaceutically acceptable salt, ester and amide derivatives thereof are disclosed having diuretic-saluretic, uricosuric and antihypertensive activity.

7 Claims, No Drawings

2,3-DIHYDRO-5-THIENYLMETHYL AND FURYLMETHYL-6-SUBSTITUTED AND 6,7-DISUBSTITUTED-BENZOFURAN-2-CARBOXYLIC ACID

BACKGROUND OF THE INVENTION

This invention relates to certain benzofurans having diuretic-saluretic, uricosuric and antihypertensive pharmacological activity. Further, this invention relates to processes for the preparation of such compounds; pharmacological compositions comprising such compounds; and to methods of treatment comprising administering such compounds and compositions to patients (both human and animal) for the alleviation os symptoms associated with electrolyte imbalance and fluid retention such as edema associated with hypertension.

The compounds of this invention may be represented by the following generic structure:

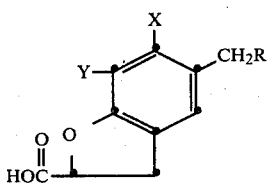

wherein
X is halo (chloro, fluoro, bromo or iodo);
Y is hydrogen, halo (chloro, fluoro, bromo or iodo) or methyl; R is

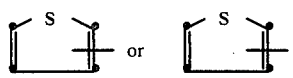

Also within the scope of the present invention are the pharmaceutically acceptable salt, ester and amide derivatives of the above described compounds.

For convenience, these compounds will be collectively referred to as "dihydrobenzofuran acids".

The pharmacological studies show that the instant products are effective diuretic, saluretic and uricosuric agents which can be used in the treatment of conditions associated with electrolyte and fluid retention in the treatment of hypertension. These compounds are able to maintain the uric acid concentration in the body at pretreatment levels or to even effect a decrease in the uric acid concentration when administered in therapeutic dosages in conventional vehicles.

Many of the presently available diuretics and saluretics have a tendency upon administration to induce hyperuricemia which may precipitate uric acid or sodium urate or both in the body which may cause from mild to severe cases of gout. The instant compounds of this invention now provide an effective tool to treat those patients (which includes humans and animals) requiring diuretic and saluretic treatment without incurring the risk of inducing gout. In fact, when used in appropriate doses, the compounds of this invention function as uricosuric agents.

Thus, it is an object of the present invention to provide the benzofurans of the above general description and to provide processes for preparation of such compounds. Further objects of this invention are to provide pharmaceutical compositions comprising such benzofurans and to provide methods of treatment comprising administering such compounds and compositions.

DETAILED DESCRIPTION OF THE INVENTION

For purposes of description, the benzofurans of the present invention (Formula I above) may be represented according to the following structural formula:

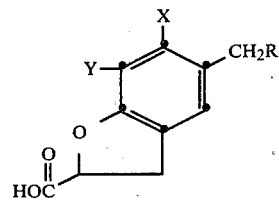

wherein X, Y and R are previously defined.

The preferred benzofurans of the present invention are those compounds of Formula I wherein X is halo, preferably chloro, or methyl and Y is halo, preferably chloro or methyl, and the pharmaceutically acceptable salts thereof.

Still more preferred benzofurans of the present invention are those compounds of Formula II below

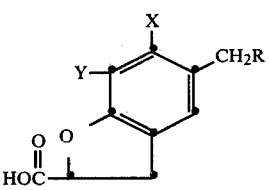

wherein
X is chloro and
Y is chloro, and
R is as defined for the more preferred benzofurans above, and
the pharmacologically acceptable salts thereof.

Several examples of specific compounds of this invention are 6,7-dichloro-2,3-dihydro-5-(2-thienylmethyl)benzofuran-2-carboxylic acid;

6,7-dichloro-2,3-dihydro-5-(2-furylmethyl)benzofuran-2-carboxylic acid.

The preferred groups of compounds depicted above have especially good diuretic, saluretic, uricosuric and antihypertensive pharmacological activity.

The compounds of Formula I can be prepared according to the following reaction scheme:

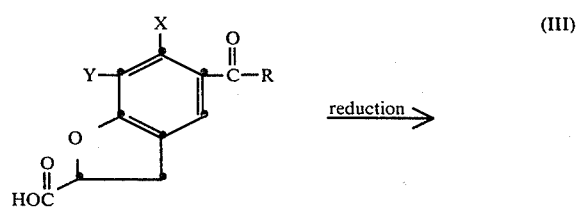

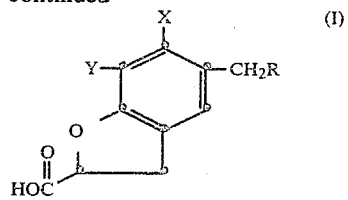

The reduction is carried out by reacting compounds of Formula I with a reducing agent preferably a reducing agent such as zinc amalgam.

The reaction is generally carried out in an inert solvent such as for example benzene, toluene and the like.

The temperature to which the reaction is carried out is 50° to 120° C. but preferably at the reflux temperature of the solvent.

When the reduction is complete the desired product (II) can be isolated from the reaction mixture by known methods.

The starting materials (III) and processes for their preparation are described in Belgian Pat. No. 594,839 patented on Dec. 12, 1976.

As previously mentioned, the nontoxic, pharmacologically acceptable salts of the acids of Formula I and II are within the scope of this invention. These salts include those of alkali metals, alkaline earth metals and mines such as ammonia, primary and secondary amines and quaternary ammonium hydroxides. Especially preferred metal cations are those derived from alkali metals, e.g., sodium, potassium, lithium, and the like and alkaline earth metals, e.g., calcium, magnesium, and the like and other metals, e.g., aluminum, iron and zinc.

Pharmaceutically acceptable salts can be formed from ammonia, primary, secondary, or tertiary amines, or quaternary ammonium hydroxides such as methylamine, dimethylamine, trimethylamine, ethylamine, N-methylhexylamine, benzylamine, α-phenethylamine, ethylenediamine, piperidine, 1-methylpiperazine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, teramethylammonium hydroxide, tetrethylammonium hydroxide, benzyltrimethylammonium and the like. These salts are particularly useful as parenteral solutions because they are very soluble in pharmaceutical carriers such as water or alcohol.

Also included within the scope of this invention are the ester and amide derivatives of the instant products which are prepared by conventional methods well known to those skilled in the art. Thus, for example, the ester derivative may be prepared by the reaction of a dihydrobenzofuran-2-carboxylic acid of this invention with an alcohol, for example, with a lower alkanol such as methanol or ethanol. The amide derivatives may be prepared by converting the same acid to its corresponding acid chloride by treatment with thionyl chloride followed by treating said acid chloride with ammonia, an appropriate mono-lower alkylamine, di-lower alkyl amine or a hetero amine, such as piperidine, morpholine and the like, to produce the corresponding amide compound. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding free acids of the present invention.

Of the nontoxic pharmaceutically acceptable salt, ester and amide derivatives of Formulae I and II, the preferred salts are those of ammonia, amines and of the alkali metals—principally sodium and potassium; the preferred esters are those derived from lower alkanols having from 1 to about 6 carbon atoms; the preferred amides are those derived from mono- and di-lower alkyl amines and hetero amines such as piperidine, morpholine and the like.

The instant compounds disclosed herein contain asymmetric carbon atom at position 2 of the benzofuran ring. The enantiomers may be separated by methods well known to those skilled in the art. This invention, therefore embraces not only the racemic benzofurans but also the optically active enantiomers. In general, the pure enantiomers are prepared by fractional crystallization of salts of the racemic acids derived from optically active amines followed by generation of the free acid of the enantiomer by addition of an equimolar amount of a strong acid such as hydrochloric acid. Several specific isomers are (+) 6,7-dichloro-2,3-dihydro-5-(2-thienylmethyl)benzofuran-2-carboxylic acid and (−) 6,7-dichloro-2,3-dihydro-5-(2-thienylmethyl)benzofuran-2-carboxylic acid.

The examples which follow illustrate the benzofuran products of the present invention and the methods by which they are prepared. However, the examples are illustrative only and it will be apparent to those having ordinary skill in the art that all the products embraced by the above-given description of the present invention may also be prepared in an analogous manner by substituting the appropriate starting materials for those set forth in the examples.

EXAMPLE 1

6,7-Dichloro-2,3-dihydro-5-(2-thienylmethyl)benzofuran-2-carboxylic acid

To a well stirred mixture of 6,7-dichloro-2,3-dihydro-5-(2-thienylcarbonyl)benzofuran-2-carboxylic acid (5 g.) in toluene (20 ml) and 6NHCl (25 ml) is added the Zn(Hg) prepared from mossy zinc (60 g), HgCl (6 g), 12NHCl (3 ml) and H$_2$O (75 ml). The reaction mixture is stirred at reflux for 4 hours. 12NHCl (12.5 ml) is added and the refluxing is continued for 14 hours. The reaction mixture is decanted from the excess Zn(Hg) and extracted with ether (3 × 100 ml). The ether extract is washed with brine (4 × 50 ml), dried over MgSO$_4$ and the ether distilled at reduced pressure. The 6,7-dichloro-2,3-dihydro-5-(2-thienylmethyl)benzofuran-2-carboxylic acid melts at 167°–9° C. after chromatography on a silica gel column using benzene-dioxane-acetic acid (25/5/1) as the eluent.

Elemental analysis for $C_{14}H_{10}Cl_2O_3S$: Calc.: C, 51.07; H, 3.06; Found: C, 50.93; H, 3.25.

What is claimed is:

1. A compound having the formula:

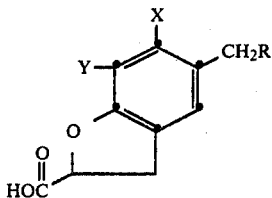

wherein
X is halo;
Y is halo, hydrogen or methyl; and
R is

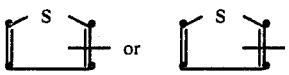

or a 5 or 6 membered heterocyclic ring containing one atom of sulfur or a substituted 5 or 6 membered heterocyclic ring containing one atom of sulfur wherein the substitutent is halo or methyl, and the nontoxic pharmaceutically acceptable salt, ester and amide derivative thereof.

2. A compound of the formula

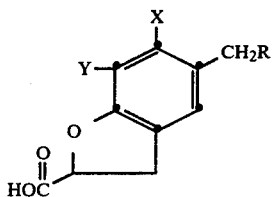

wherein
X is chloro;
Y is chloro;
R is selected from the group consisting of 2-thienyl or 3-thienyl; and
the nontoxic pharmaceutically acceptable salt derivative thereof.

3. The compound of claim 2 which is 6,7-dichloro-2,3-dihydro-5-(2-thienylmethyl)benzofuran-2-carboxylic acid.

4. The compound of claim 1 which is 6,7-dichloro-2,3-dihydro-5-(2-furylmethyl)benzofuran-2-carboxylic acid.

5. The (+) and (−) isomers of the compound of claim 2.

6. A pharmaceutical composition useful in the treatment of edema and hypertension comprising a therapeutically effective amount of a compound of the formula of

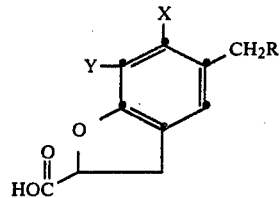

wherein
X is halo;
Y is halo, hydrogen or methyl; and
R is

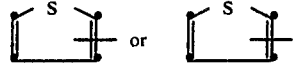

or a 5 to 6 membered heterocyclic ring containing one atom of sulfur or a substituted 5 or 6 membered heterocyclic ring containing one atom of sulfur wherein the substitutent is halo or methyl, and the nontoxic pharmaceutically acceptable salt, ester and amide derivative thereof along with a pharmaceutically acceptable carrier.

7. A method of treatment of edema associated with hypertension comprising the administration of a therapeutically effective amount in unitary dosage form of a compound having the formula of:

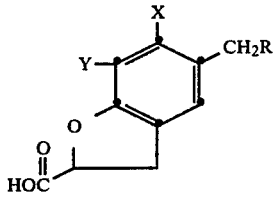

wherein
X is halo;
Y is halo, hydrogen or methyl; and
R is

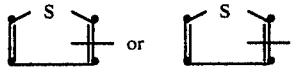

or a 5 or 6 membered heterocyclic ring containing one atom of sulfur or a substituted 5 or 6 membered heterocyclic ring containing one atom of sulfur wherein the substitutent is halo or methyl, and the nontoxic pharmaceutically acceptable salt, ester and amide derivative thereof.

* * * * *

UNITED STATES PATENT OFFICE
CERTIFICATE OF CORRECTION

PATENT NO. : 4,189,496
DATED : Feb. 19, 1980
INVENTOR(S) : EDWARD J. CRAGOE, JR. et al

It is certified that error appears in the above-identified patent and that said Letters Patent are hereby corrected as shown below:

Col. 1, Lines 35-40;
Col. 5, lines 15-20; Col. 6, lines 15-20 and Col. 6 lines 45-50 the second structure should read:

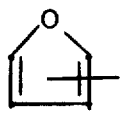

Signed and Sealed this

Third Day of June 1980

[SEAL]

*Attest:*

*Attesting Officer*

SIDNEY A. DIAMOND

*Commissioner of Patents and Trademarks*